US006593117B2

(12) United States Patent
Kawasaki et al.

(10) Patent No.: US 6,593,117 B2
(45) Date of Patent: Jul. 15, 2003

(54) GMP SYNTHETASE AND GENE CODING FOR THE SAME

(75) Inventors: Hisashi Kawasaki, Kawasaki (JP);
Yoshihiro Usuda, Kawasaki (JP);
Yasuhiro Mihara, Kawasaki (JP);
Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/767,878

(22) Filed: Jan. 24, 2001

(65) Prior Publication Data

US 2002/0151023 A1 Oct. 17, 2002

Related U.S. Application Data

(62) Division of application No. 09/550,338, filed on Apr. 14, 2000, now Pat. No. 6,210,951.

(30) Foreign Application Priority Data

Apr. 22, 1999 (JP) .......................................... 11-114787

(51) Int. Cl.[7] .............................. C12N 9/00; C12N 1/20; C12N 15/00; C07K 1/00; C07H 21/04

(52) U.S. Cl. ..................... 435/183; 435/252.3; 435/325; 435/320.1; 530/350; 536/23.2

(58) Field of Search .............................. 435/183, 320.1, 435/325, 252.3; 530/350; 536/23.2

(56) References Cited

U.S. PATENT DOCUMENTS 5,789,216 A * 8/1998 Lou et al. ................... 435/183

FOREIGN PATENT DOCUMENTS

KR 96-7743 6/1996

OTHER PUBLICATIONS

Yonetani, GenEmbl Database, Accession No. AB003155, Jan. 2000.*
Han et al., GenEmbl Database, Accession No. Y10499, Jan. 1998.*
P. Mantsalas et al., "Cloning and sequence of *Bacillus subtilis* purA and guaA, involved in the conversion of IMP to AmP and GMP" J. Bacteriol. 174, pp. 1883–1890, Apr. 26, 1993.
J. K. Han, Unpublished, Submitted Jan. 13, 1997 to the EMBL/GenBank/DDBJ databases, "*B.Ammoniagenes* guaA gene" Jan. 8, 1998.
Michiel M. Van Lookeren Campagne et al., "Functional Cloning of a Dietyostelium Discoideum cDNA Encoding GMP Synthetase", The Journal of Biological Chemistry, vol. 266, No. 25, Issue Sep. 5, pp 16448–16452, (1991).
Van Lookeren Campagne et al., "Functional cloning of a Dicyostelium discoideum cDNA encoding GMP synthetase", J. Biol. Chem. 266, pp. 16448–16452 (1991).
N. Margolis et al., "Plasmid Location of Borrelia Purine Biosynthesis Gene Homologs", Journal of Bacteriology, Nov. 1994, vol. 176(1) pp. 6427–6432
Cole et al., "Deciphering the biology of *Mycobacterium tuberculosis* from the complete genome sequence", Nature, vol. 393, pp. 537–544, Jun. 1, 1998.
P. Mantsala et al., "Cloning and Sequence of *Bacillus subtilis* purA and guaA, Involved in the Conversion of IMP to AMP and GMP", vol. 174(6) Journal of Bacteriology, Mar. (1992), pp. 1883–1890.

* cited by examiner

*Primary Examiner*—M. Monshipouri
(74) *Attorney, Agent, or Firm*—Oblon, Spivak, McClelland, Maier & Neustadt, P.C.

(57) ABSTRACT

A protein which has a GMP synthetase activity, a DNA which codes for the protein and a transformant which is introduced with the DNA in a form that allows expression of the protein encoded by the DNA.

7 Claims, 1 Drawing Sheet

SEQUENCE LISTING

<160> NUMBER OF SEQ ID NOS: 13

<210> SEQ ID NO 1
<211> LENGTH: 3390
<212> TYPE: DNA
<213> ORGANISM: Brevibacterium lactofermentum (Corneybacterium
      glutamicum)
<220> FEATURE:
<221> NAME/KEY: CDS
<222> LOCATION: (887)..(2455)

<400> SEQUENCE: 1

```
gaattccacc gcctgggaac gattacagca gtggcggaat ctatgaacta cagtcgttct      60
gcgatctccc aacaaatggc gctgctggaa aaagaaattg gtgtgaaact ctttgaaaaa     120
agcggccgaa acctctactt cacagaacaa ggcgaagtgt tggcctcaga aacacatgcg     180
atcatggcag cagtcgatca cgcccgcgca gccgtcctag attcgatgtc tgaagtatcc     240
ggaacgctga aagtcacctc cttccaatcc ctgctgttca cccttgcccc gaaagccatc     300
gcgcgcctga ccgagaaata cccacacctg caagtagaaa tctcccaact agaagtcacc     360
gcagcgctcg aagaactccg cgcccgccgc gtcgacgtcg cactcggtga ggaataccccc     420 gtggaagttc ccctcgttga tgccagcatt caccgcgaag tcctcttcga agacccatg     480 ctgctggtca cccagaaag cggtccatac tccggcctca ccctgccaga actccgcgac     540
atccccatcg ccatcgaccc gcccgacctc cccgcaggcg aatgggtcca taggctctgc     600
cggcgcgccg ggtttgagcc ccgcgtgacc tttgaaacca gcgatcccat gctccaggca     660
cacctcgtgc gcagcggttt ggccgtgaca ttttccccca cactgctcac cccgatgctg     720
gaaggcgtgc acatccagcc gctgcccggc aaccccacgc gcacgctcta caccgcggtc     780
agggaagggc gccagaggca tccagccatt aaagcttttc gacgaaccct ccgcccatgt     840
ggccaaagaa tcttatttgg aggctcgtct agtagagtga gttctt gtg agc ctt         895
                                                    Val Ser Leu
                                                     1 cag aca aat cat cgc cca gta ctc gtc gtt gac ttc ggc gca cag tac        943
Gln Thr Asn His Arg Pro Val Leu Val Val Asp Phe Gly Ala Gln Tyr
      5                  10                  15 gcg cag ctg atc gca cgt cgt gtg cgt gag gcc ggc atc tac tcc gaa        991
Ala Gln Leu Ile Ala Arg Arg Val Arg Glu Ala Gly Ile Tyr Ser Glu
```

-continued

```
          20                  25                  30                  35 gtc atc ccg cac acc gcc acc gca gac gat gtg cgc gct aaa aat gca        1039
Val Ile Pro His Thr Ala Thr Ala Asp Asp Val Arg Ala Lys Asn Ala
                40                  45                  50 gca gcc ctc gtc ctt tcc ggt ggt cca tcc tcc gtg tat gcc gag gga        1087
Ala Ala Leu Val Leu Ser Gly Gly Pro Ser Ser Val Tyr Ala Glu Gly
            55                  60                  65 gca cca tcc ctt gac gct gag atc cta gat ctc gga ttg cca gta ttt        1135
Ala Pro Ser Leu Asp Ala Glu Ile Leu Asp Leu Gly Leu Pro Val Phe
        70                  75                  80 ggc att tgc tac ggc ttc caa gcc atg acc cac gcg ctt ggt ggc acc        1183
Gly Ile Cys Tyr Gly Phe Gln Ala Met Thr His Ala Leu Gly Gly Thr
    85                  90                  95 gtt gcc aac acc ggt aag cgc gaa tac gga cgc acc gac atc aac gtt        1231
Val Ala Asn Thr Gly Lys Arg Glu Tyr Gly Arg Thr Asp Ile Asn Val
100                 105                 110                 115 gcc ggt ggc gtc ctc cac gaa ggc ctc gag gcc tgc cac aag gtg tgg        1279
Ala Gly Gly Val Leu His Glu Gly Leu Glu Ala Cys His Lys Val Trp
                120                 125                 130 atg agc cac ggc gac gcc gtc tct gaa gcc cca gaa ggt ttc gta gtc        1327
Met Ser His Gly Asp Ala Val Ser Glu Ala Pro Glu Gly Phe Val Val
            135                 140                 145 acc gct tcc tcc gaa ggt gcg cct gtc gca gct ttc gaa aac aag gaa        1375
Thr Ala Ser Ser Glu Gly Ala Pro Val Ala Ala Phe Glu Asn Lys Glu
        150                 155                 160 cgc aaa atg gct ggc gtg cag tac cac cct gag gtg ctg cac tca cca        1423
Arg Lys Met Ala Gly Val Gln Tyr His Pro Glu Val Leu His Ser Pro
    165                 170                 175 cac ggc cag gca gtt ctg acc cgc ttc ctc act gag atc gca ggt cta        1471
His Gly Gln Ala Val Leu Thr Arg Phe Leu Thr Glu Ile Ala Gly Leu
180                 185                 190                 195 gag cag aac tgg acc gca gca aac atc gct gaa gaa ctc atc gaa aag        1519
Glu Gln Asn Trp Thr Ala Ala Asn Ile Ala Glu Glu Leu Ile Glu Lys
                200                 205                 210 gtc cgc gag cag atc ggc gaa gat ggc cgc gct att tgt ggc cta tcc        1567
Val Arg Glu Gln Ile Gly Glu Asp Gly Arg Ala Ile Cys Gly Leu Ser
            215                 220                 225 ggt ggt gtg gac tcc gct gtt gcc ggt gct ttg gtg cag cgt gca att        1615
Gly Gly Val Asp Ser Ala Val Ala Gly Ala Leu Val Gln Arg Ala Ile
        230                 235                 240 ggt gac cgt ttg acc tgt gtc ttt gtt gac cac ggt ctg ctg cgt gcc        1663
Gly Asp Arg Leu Thr Cys Val Phe Val Asp His Gly Leu Leu Arg Ala
    245                 250                 255 ggt gag cgc gag cag gtg gaa aaa gac ttc gtc gca gca acc ggc gcc        1711
Gly Glu Arg Glu Gln Val Glu Lys Asp Phe Val Ala Ala Thr Gly Ala
260                 265                 270                 275 aag ctg gtt acc gtt gat gag cgt caa gca ttc ctg tcc aag ctg gcc        1759
Lys Leu Val Thr Val Asp Glu Arg Gln Ala Phe Leu Ser Lys Leu Ala
                280                 285                 290 gga gtt acc gaa cca gaa gca aag cgc aag gct atc ggc gct gag ttc        1807
Gly Val Thr Glu Pro Glu Ala Lys Arg Lys Ala Ile Gly Ala Glu Phe
            295                 300                 305 atc cgc tcc ttc gag cgc gca gtt gcc ggt gtg ctg gaa gat gca cca        1855
Ile Arg Ser Phe Glu Arg Ala Val Ala Gly Val Leu Glu Asp Ala Pro
        310                 315                 320 gaa ggt tcc acc gtg gac ttc cta gtt cag ggc acc ctg tac cca gac        1903
Glu Gly Ser Thr Val Asp Phe Leu Val Gln Gly Thr Leu Tyr Pro Asp
    325                 330                 335 gtc gtg gaa tcc ggt ggt gga tct ggt acc gca aac atc aag agc cac        1951
```

-continued

| | | | | | | | | | | | | |
|---|---|---|---|---|---|---|---|---|---|---|---|---|
| Val | Val | Glu | Ser | Gly | Gly | Gly | Ser | Gly | Thr | Ala | Asn | Ile | Lys | Ser | His |
| 340 | | | | 345 | | | | | 350 | | | | | 355 | |

```
tac aac gtc ggt gga ctg cca gac gat gtg gaa ttc aag ctt gtt gag    1999
Tyr Asn Val Gly Gly Leu Pro Asp Asp Val Glu Phe Lys Leu Val Glu
            360                 365                 370 cca ctg cgt gac ctc ttc aaa gac gaa gtc cgt gcc gtt ggc cgt gaa    2047
Pro Leu Arg Asp Leu Phe Lys Asp Glu Val Arg Ala Val Gly Arg Glu
            375                 380                 385 ctt ggc ctg cct gag gaa atc gtt ggc cgc cag cca ttc cca gga cca    2095
Leu Gly Leu Pro Glu Glu Ile Val Gly Arg Gln Pro Phe Pro Gly Pro
            390                 395                 400 gga ctt ggt atc cgc atc atc ggt gaa gtc acc gaa gag cgc ctg gaa    2143
Gly Leu Gly Ile Arg Ile Ile Gly Glu Val Thr Glu Glu Arg Leu Glu
        405                 410                 415 acc ctc cgc cac gct gac ctg atc gcc cgc acc gag ctc acc gaa gcc    2191
Thr Leu Arg His Ala Asp Leu Ile Ala Arg Thr Glu Leu Thr Glu Ala
420                 425                 430                 435 gga ctc gac ggc gtg atc tgg cag tgc cca gtc gtc ctc ttg gca gat    2239
Gly Leu Asp Gly Val Ile Trp Gln Cys Pro Val Val Leu Leu Ala Asp
                440                 445                 450 gtc cgc tct gtt gga gtc caa ggt gac ggc cgc acc tac gga cac cca    2287
Val Arg Ser Val Gly Val Gln Gly Asp Gly Arg Thr Tyr Gly His Pro
            455                 460                 465 atc gtg ctg cgc cca gta tct tcc gaa gac gca atg acc gcc gac tgg    2335
Ile Val Leu Arg Pro Val Ser Ser Glu Asp Ala Met Thr Ala Asp Trp
        470                 475                 480 acc cgc ttg cca tac gaa gtc ctg gag aag atc tcc acc cgc atc acc    2383
Thr Arg Leu Pro Tyr Glu Val Leu Glu Lys Ile Ser Thr Arg Ile Thr
    485                 490                 495 aac gaa gtt cca gac gta aac cgc gtg gtt ttg gac gta acc tcc aag    2431
Asn Glu Val Pro Asp Val Asn Arg Val Val Leu Asp Val Thr Ser Lys
500                 505                 510                 515 cca cca gga acc atc gaa tgg gag taggccttaa atgagccttc gttaagcggc    2485
Pro Pro Gly Thr Ile Glu Trp Glu
                520
```

| | |
|---|---|
| aatcaccta tcggtgattg ccgctttccc atttctccgg gttttctgga acttttggg | 2545 |
| cgtatgctgg gaatgatctt attattttga tttcagaaag caggagagac cagatgagcg | 2605 |
| aaatccttga aacctactgg gcaccccact tcggaaacac cgatgaagcc gcagcactcg | 2665 |
| tttcatactt ggcacaagct tccggtgatc ctattgaggt tcacaccctg ttcggggatt | 2725 |
| taggtttaga cggactctct ggaaactaca ccgacactga gatcgacggc tacggcgacg | 2785 |
| cattcctgct ggttgcagca ctagcagtgt tgatggctga aaacaaagca tccggcggcg | 2845 |
| tgaatctggg tgaagttggg ggagctgata aatcgatccg gctgcatgtt gaatccaagg | 2905 |
| aaaacaccca gatcaacacc gcattgaagt actttgcgct ttccccagaa gaccacgcag | 2965 |
| cggcagatcg cttcgatgag gatgacctgt ctgagcttgc caacttgagt gaagagctgc | 3025 |
| gcggacagct ggactaattg ctgcccgttt aaggagtccg attcttcaga tgagtagatg | 3085 |
| cctccaagtg aggctgggag gctcttagaa tcgattctga gagggcactt tttattggcc | 3145 |
| ttggggtgga atctgcaacg gaccaaacca cactgcccac ggatcctaaa aagggggatcc | 3205 |
| gtgggcagtc tggtttggtt attcgacctt caaaccggtc acacatgccc acgaacccca | 3265 |
| ataatcggat tcgtgggcac tctggtttgg ttaccaggat gggttagtca ttctgatcag | 3325 |
| cgaattccac gttcacatcg ccaattccag agttcacaac cagattcagc attggacctt | 3385 |
| ctaga | 3390 |

```
<210> SEQ ID NO 2
<211> LENGTH: 523
<212> TYPE: PRT
<213> ORGANISM: Brevibacterium lactofermentum (Corneybacterium
      glutamicum)

<400> SEQUENCE: 2
```

Val Ser Leu Gln Thr Asn His Arg Pro Val Leu Val Asp Phe Gly
1               5                   10                  15

Ala Gln Tyr Ala Gln Leu Ile Ala Arg Arg Val Arg Glu Ala Gly Ile
            20                  25                  30

Tyr Ser Glu Val Ile Pro His Thr Ala Thr Ala Asp Asp Val Arg Ala
        35                  40                  45

Lys Asn Ala Ala Ala Leu Val Leu Ser Gly Gly Pro Ser Ser Val Tyr
    50                  55                  60

Ala Glu Gly Ala Pro Ser Leu Asp Ala Glu Ile Leu Asp Leu Gly Leu
65                  70                  75                  80

Pro Val Phe Gly Ile Cys Tyr Gly Phe Gln Ala Met Thr His Ala Leu
                85                  90                  95

Gly Gly Thr Val Ala Asn Thr Gly Lys Arg Glu Tyr Gly Arg Thr Asp
            100                 105                 110

Ile Asn Val Ala Gly Gly Val Leu His Glu Gly Leu Glu Ala Cys His
        115                 120                 125

Lys Val Trp Met Ser His Gly Asp Ala Val Ser Glu Ala Pro Glu Gly
    130                 135                 140

Phe Val Val Thr Ala Ser Ser Glu Gly Ala Pro Val Ala Ala Phe Glu
145                 150                 155                 160

Asn Lys Glu Arg Lys Met Ala Gly Val Gln Tyr His Pro Glu Val Leu
                165                 170                 175

His Ser Pro His Gly Gln Ala Val Leu Thr Arg Phe Leu Thr Glu Ile
            180                 185                 190

Ala Gly Leu Glu Gln Asn Trp Thr Ala Ala Asn Ile Ala Glu Glu Leu
        195                 200                 205

Ile Glu Lys Val Arg Glu Gln Ile Gly Glu Asp Gly Arg Ala Ile Cys
    210                 215                 220

Gly Leu Ser Gly Gly Val Asp Ser Ala Val Ala Gly Ala Leu Val Gln
225                 230                 235                 240

Arg Ala Ile Gly Asp Arg Leu Thr Cys Val Phe Val Asp His Gly Leu
                245                 250                 255

Leu Arg Ala Gly Glu Arg Glu Gln Val Glu Lys Asp Phe Val Ala Ala
            260                 265                 270

Thr Gly Ala Lys Leu Val Thr Val Asp Glu Arg Gln Ala Phe Leu Ser
        275                 280                 285

Lys Leu Ala Gly Val Thr Glu Pro Glu Ala Lys Arg Lys Ala Ile Gly
    290                 295                 300

Ala Glu Phe Ile Arg Ser Phe Glu Arg Ala Val Ala Gly Val Leu Glu
305                 310                 315                 320

Asp Ala Pro Glu Gly Ser Thr Val Asp Phe Leu Val Gln Gly Thr Leu
                325                 330                 335

Tyr Pro Asp Val Val Glu Ser Gly Gly Ser Gly Thr Ala Asn Ile
            340                 345                 350

Lys Ser His Tyr Asn Val Gly Gly Leu Pro Asp Val Glu Phe Lys
        355                 360                 365

Leu Val Glu Pro Leu Arg Asp Leu Phe Lys Asp Glu Val Arg Ala Val

```
                        370                 375                 380
Gly Arg Glu Leu Gly Leu Pro Glu Glu Ile Val Gly Arg Gln Pro Phe
385                 390                 395                 400

Pro Gly Pro Gly Leu Gly Ile Arg Ile Ile Gly Glu Val Thr Glu Glu
                405                 410                 415

Arg Leu Glu Thr Leu Arg His Ala Asp Leu Ile Ala Arg Thr Glu Leu
            420                 425                 430

Thr Glu Ala Gly Leu Asp Gly Val Ile Trp Gln Cys Pro Val Val Leu
        435                 440                 445

Leu Ala Asp Val Arg Ser Val Gly Val Gln Gly Asp Gly Arg Thr Tyr
    450                 455                 460

Gly His Pro Ile Val Leu Arg Pro Val Ser Ser Glu Asp Ala Met Thr
465                 470                 475                 480

Ala Asp Trp Thr Arg Leu Pro Tyr Glu Val Leu Glu Lys Ile Ser Thr
                485                 490                 495

Arg Ile Thr Asn Glu Val Pro Asp Val Asn Arg Val Val Leu Asp Val
                500                 505                 510

Thr Ser Lys Pro Pro Gly Thr Ile Glu Trp Glu
            515                 520

<210> SEQ ID NO 3
<211> LENGTH: 15
<212> TYPE: DNA
<213> ORGANISM: Artificial/Unknown
<220> FEATURE:
<221> NAME/KEY: misc_feature
<222> LOCATION: (1)..()
<223> OTHER INFORMATION: w=a or t
<221> NAME/KEY: misc_feature
<222> LOCATION: (13)..()
<223> OTHER INFORMATION: r=g or a
<221> NAME/KEY: misc_feature
<222> LOCATION: (7)..()
<223> OTHER INFORMATION: w=a or t
<221> NAME/KEY: misc_feature
<222> LOCATION: ()..()
<223> OTHER INFORMATION: synthetic DNA

<400> SEQUENCE: 3
wtcccawtcg atrgt                                                    15

<210> SEQ ID NO 4
<211> LENGTH: 15
<212> TYPE: DNA
<213> ORGANISM: Artificial/Unknown
<220> FEATURE:
<221> NAME/KEY: misc_feature
<222> LOCATION: (12)..()
<223> OTHER INFORMATION: y=t or c
<221> NAME/KEY: misc_feature
<222> LOCATION: (15)..()
<223> OTHER INFORMATION: y=t or c
<221> NAME/KEY: misc_feature
<222> LOCATION: ()..()
<223> OTHER INFORMATION: synthetic DNA

<400> SEQUENCE: 4
caccacaacg tyggy                                                    15

<210> SEQ ID NO 5
<211> LENGTH: 14
<212> TYPE: DNA
<213> ORGANISM: Artificial/Unknown
<220> FEATURE:
<221> NAME/KEY: misc_feature
```

```
<222> LOCATION: (1)..()
<223> OTHER INFORMATION: r=g or a
<221> NAME/KEY: misc_feature
<222> LOCATION: (4)..()
<223> OTHER INFORMATION: r=g or a
<221> NAME/KEY: misc_feature
<222> LOCATION: ()..()
<223> OTHER INFORMATION: synthetic DNA

<400> SEQUENCE: 5
rccracgttg ggtg                                                           14

<210> SEQ ID NO 6
<211> LENGTH: 15
<212> TYPE: DNA
<213> ORGANISM: Artificial/Unknown
<220> FEATURE:
<221> NAME/KEY: misc_feature
<222> LOCATION: (9)..()
<223> OTHER INFORMATION: y=t or c
<221> NAME/KEY: misc_feature
<222> LOCATION: (15)..()
<223> OTHER INFORMATION: y=t or c
<221> NAME/KEY: misc_feature
<222> LOCATION: ()..()
<223> OTHER INFORMATION: synthetic DNA

<400> SEQUENCE: 6
tggatgtcyc acggy                                                          15

<210> SEQ ID NO 7
<211> LENGTH: 16
<212> TYPE: DNA
<213> ORGANISM: Artificial/Unknown
<220> FEATURE:
<221> NAME/KEY: misc_feature
<222> LOCATION: (16)..()
<223> OTHER INFORMATION: y=t or c
<221> NAME/KEY: misc_feature
<222> LOCATION: ()..()
<223> OTHER INFORMATION: synthetic DNA

<400> SEQUENCE: 7
ttggatgagc cacggy                                                         16

<210> SEQ ID NO 8
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 8
tgctctagac ctgcgatctc agtgaggaag                                          30

<210> SEQ ID NO 9
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 9
cagggtggta ctgcacgcca gccattttgc                                          30
```

```
<210> SEQ ID NO 10
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 10
ctctgttgga gtccaaggtg acggccgcag                                    30

<210> SEQ ID NO 11
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 11
gtatcttccg aagacgcaat gaccgccgac                                    30

<210> SEQ ID NO 12
<211> LENGTH: 49
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 12
ctcgtcgaca aggaaaaaga cgtatgagcc ttcagacaaa tcatcgccc               49

<210> SEQ ID NO 13
<211> LENGTH: 52
<212> TYPE: DNA
<213> ORGANISM: Artificial/Unknown
<220> FEATURE:
<221> NAME/KEY: misc_feature
<222> LOCATION: ()..()
<223> OTHER INFORMATION: synthetic DNA

<400> SEQUENCE: 13
ctcgcatgct taatcccatt cgatggttcc tggtggcttg gaggttacgt cc           52
```

GMP SYNTHETASE AND GENE CODING FOR THE SAME

CROSS-REFERENCE TO A RELATED APPLICATION

This application is a Divisional Application of U.S. Ser. No. 09/550,338, which was filed Apr. 14, 2000, now U.S. Pat. No. 6,210,951

BACKGROUND OF THE INVENTION

1. Field of the Invention

The present invention relates to a novel GMP synthetase and a DNA that codes for it. A microorganism that has GMP synthetase and its enzymatic activity can be used for the production of nucleic acid compounds such as guanosine 5'-monophosphate, which is useful as a raw material of seasonings and so forth.

2. Description of the Related Art

In the conventional production of nucleic acid compounds such as guanosine 5'-monophosphate (also called 5'-guanylic acid, hereinafter abbreviated as "GMP") and guanosine by fermentation, mutant strains that are imparted with adenine auxotrophy and nucleic acid analogue resistance have been utilized in a medium containing a limited amount of adenine compounds (Japanese Patent Publication (Kokoku) Nos. 55-2956/1980 and 55-45199/1980).

Usual mutagenesis treatments often introduce mutations in genes of resulting mutant strains other than a target gene. In addition, because complicated controlling mechanisms are present in the biosynthetic pathways of nucleic acid compounds, it is difficult to obtain a microorganism that produces a marked amount of a certain nucleic acid compound. Therefore, mutant strains obtained by conventional methods for breeding bacterial strains have not necessarily been satisfactory strains.

GMP is synthesized by an amination reaction catalyzed by GMP synthetase and utilizing L-glutamine as an amino group donor from 5'-inosinic acid (IMP) via xanthylic acid (XMP). Therefore, there has been proposed a method for producing GMP which utilizes *Escherichia coli* transformed with a GMP synthetase gene (guaA) of *Escherichia coli* (Japanese Patent Publication (Kokoku) No. 7-16431/1995). The guaA gene has been isolated from *Bacillus subtilis* (*J. Bacteriol.*, 174, 1883–1890 (1992), EMBL/GenBank/DDBJ Accession M83691), *Corynebacterium ammoniagenes* (Korean Patent Publication No. 96-7743, EMBL/GenBank/ DDBJ Accession Y10499), *Borrelia burgdorferi* (*J. Bacteriol.*, 176, 6427–6432 (1994), EMBL/GenBank/DDBJ Accession L25883), *Dictyostelium discoideum* (*J. Biol. Chem.*, 266, 16448–16452 (1991), EMBL/GenBank/DDBJ Accession M64282) and so forth.

However, no guaA gene of *Brevibacterium lactotermentum* (*Corynebacterium glutamicum*) has been known.

SUMMARY OF THE INVENTION

An object of the present invention is to provide a guaA gene of *Brevibacterium lactofermentum* (*Corynebacterium glutamicum*) and a transformant introduced with the gene.

The inventors of the present invention actively studied in order to achieve the aforementioned object. As a result, they found a plurality of regions conserved in amino acid sequences deduced from the known guaA genes, and based on the amino acid sequences of these regions, selected a region and a sequence suitable for amplifying a guaA gene of *Brevibacterium lactofermentum* (*Corynebacterium glutamicum*) by PCR. Then, they successfully isolated a part of the guaA gene by utilizing the selected sequence, and further obtained the guaA gene in its full length. Thus, they accomplished the present invention.

That is, the present invention provides the followings.
(1) A protein defined in the following (A) or (B):
 (A) a protein which has the amino acid sequence of SEQ ID NO: 2, or
 (B) a protein which has the amino acid sequence of SEQ ID NO: 2 including substitution, deletion, insertion, addition or inversion of one or several amino acids, and has GMP synthetase activity.
(2) A DNA which codes for a protein defined in the following (A) or (B):
 (A) a protein which has the amino acid sequence of SEQ ID NO: 2, or
 (B) a protein which has the amino acid sequence of SEQ ID NO: 2 including substitution, deletion, insertion, addition or inversion of one or several amino acids, and has GMP synthetase activity.
(3) The DNA according to (2), which is a DNA defined in the following (a) or (b):
 (a) a DNA which has the nucleotide sequence comprising at least the nucleotide sequence of the nucleotide numbers 887 to 2455 in SEQ ID NO: 1; or
 (b) a DNA which is hybridizable with a nucleotide sequence comprising at least the nucleotide sequence of the nucleotide numbers 887 to 2455 in SEQ ID NO: 1 under a stringent condition, and codes for a protein having GMP synthetase activity.
(4) The DNA according to (3), wherein the stringent condition means a condition that washing is performed at 1×SSC, 0.1% SDS and 60° C.
(5) A transformant which is introduced with the DNA according to any one of (2) to (4) in a form that allows expression of a protein encoded by the DNA.

PREFERRED EMBODIMENTS OF THE INVENTION

The present invention will be explained in detail hereafter.

The DNA of the present invention is a DNA that codes for GMP synthetase derived from *Brevibacterium lactofermentum* (*Corynebacterium glutamicum*). *Brevibacterium lactofermentum* has now been unified into *Corynebacterium glutamicum*, but it may be referred to as *Brevibacterium lactofermentum* in the present specification for convenience.

A part of the DNA of the present invention can be obtained from chromosomal DNA of *Brevibacterium lactofermentum* by PCR. Primers used for the PCR can be designed as follows. That is, an amino acid sequence of a region conserved in GMP synthetases can be retrieved by alignment of amino acid sequences of the GMP synthetases deduced from nucleotide sequences of the guaA genes which have been cloned from several microorganisms, for example, *Escherichia coli*, *Bacillus subtilis*, *Corynebacterium ammoniagenes*, *Borrelia burgdorferi*, *Dictyostelium discoideum* and so forth. Then, the primers can be designed based on the retrieved conserved region. In this procedure, the PCR primers are designed by selecting such a region that the number of corresponding codons should become as few as possible, and referring to occurring frequency of the codons in *Brevibacterium lactofermentum*.

Chromosomal DNA of *B. lactofermentum* can be prepared by, for example, the method of Saito and Miura (*Biochem.*

*Biophys. Acta.*, 72, 619, (1963)), and the method of K. S. Kirby (*Biochem. J.*, 64, 405, (1956)) or the like.

As preferred primers and PCR condition for amplification of the guaA gene, the combinations of primers and the reaction conditions used for Reactions 2, 3 and 4 shown in Table 1 can be mentioned. By using these reaction conditions, reaction products having sizes of about 0.5 kbp, about 1.2 kbp and about 0.7 kbp, respectively, can be obtained. Among these reaction products, the fragment of about 1.2 kbp overlaps the fragment of about 0.5 kbp.

Based on a partial sequence of the guaA gene obtained as described above, upstream and downstream flanking regions of the partial sequence can be obtained by the cassette-ligation mediated PCR method (*Molecular and Cellular Probes*, 6, 467–475) or the like, and thus a full length guaA gene can be obtained. That is, a region flanking a known region on chromosomal DNA can be obtained by ligating a cassette to a chromosomal DNA fragment digested with a suitable restriction enzyme, and amplifying it by PCR utilizing a primer corresponding to the known region and a primer corresponding to the cassette. In this procedure, by using a dephosphorylated 5' end of the cassette, a nick is produced at the ligation site of the chromosomal DNA fragment and the 5' end of the cassette. Therefore, the DNA synthesis started from the cassette primer is stopped at this ligation site, and thus only DNA synthesized from the synthetic primer serves as a template for the synthesis from the cassette primer to form a complementary strand. The nucleotide sequence of the obtained amplification product is determined, then specific primers for the newly determined nucleotide sequence are synthesized, and PCR is performed by using the chromosomal DNA fragment similarly ligated to the cassette as a template. By repeating this procedure, the upstream and downstream flanking regions can be obtained. A kit utilizing this method is commercially available (TAKARA LA PCR in vitro Cloning Kit, Takara Shuzo), and it can be utilized for obtaining the DNA of the present invention.

Since the nucleotide sequences of the DNA of the present invention and the flanking regions have been revealed, the DNA of the present invention can be directly amplified by PCR utilizing oligonucleotides synthesized based on the nucleotide sequences as primers and chromosomal DNA of coryneform bacteria as a template. As such primers, oligonucleotides which have the nucleotide sequences shown in SEQ ID NO: 12 and SEQ ID NO: 13 can be mentioned. In a DNA obtained by using these primers, the SD (Shine-Dalgarno) sequence is added upstream of the region coding for GMP synthetase, and restriction enzyme recognition sites are added to the both ends. Moreover, the DNA of the present invention can also be isolated from a chromosomal DNA library by hybridization utilizing an oligonucleotide synthesized based on its nucleotide sequence as a probe.

An example of nucleotide sequence of a DNA fragment containing the DNA of the present invention, which can be obtained as described above, is shown in SEQ ID NO: 1 of Sequence Listing. In this nucleotide sequence, the region consisting of nucleotides of nucleotide numbers 887–2455 codes for GMP synthetase, which is the protein of the present invention.

The DNA of the present invention may code for GMP synthetase including substitution, deletion, insertion, addition, or inversion of one or several amino acids at one or a plurality of positions, provided that the activity of GMP synthetase encoded thereby is not deteriorated. The number of "several" amino acids differs depending on the position or the type of amino acid residues in the three-dimensional structure of the protein. This is because of the following reason. That is, some amino acids such as isoleucine and valine are amino acids having high homology to one another. The difference in such an amino acid does not greatly affect the three-dimensional structure of the protein. Therefore, the protein encoded by the DNA of the present invention may be one which has homology of not less than 80%, preferably 90% with respect to the entire amino acid residues for constituting. GMP synthetase, and which has the GMP synthetase activity. More appropriately, the number of "several" amino acids is 2 to 104, preferably 2 to 50, and more preferably 2 to 10.

Alternatively, DNA of the present invention may be DNA which has homology of not less than 60%, preferably not less than 70% and more preferably not less than 80% with the region consisting of nucleotides of nucleotide numbers 887–2455 in SEQ ID NO: 1 in nucleotide sequence level, provided that the protein encoded by the DNA has GMP synthetase activity.

DNA, which codes for the substantially same protein as GMP synthetase as described above, is obtained, for example, by modifying the nucleotide sequence, for example, by means of the site-directed mutagenesis method so that one or more amino acid residues at a specified site involve substitution, deletion, insertion, addition, or inversion. DNA modified as described above may be obtained by the conventionally known mutation treatment. The mutation treatment includes a method for treating DNA coding for GMP synthetase in vitro, for example, with hydroxylamine, and a method for treating a microorganism, for example, a bacterium belonging to the genus Escherichia harboring DNA coding for GMP synthetase with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutant or variant which naturally occurs, for example, on the basis of the individual difference or the difference in species or genus of the microorganism which harbors GMP synthetase The DNA, which codes for substantially the same protein as GMP synthetase, is obtained by isolating DNA which is hybridizable with DNA having, for example, a nucleotide sequence corresponding to nucleotide numbers of 887 to 2455 of the nucleotide sequence depicted in SEQ ID NO: 1 in Sequence Listing under a stringent condition, and which codes for a protein having the GMP synthetase activity, from DNA coding for GMP synthetase having mutation or from a cell harboring it. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 60% are hybridized with each other, and DNA's having homology lower than the above are not hybridized with each other. Alternatively, the stringent condition is exemplified by a condition in which washing in hybridization procedure is performed at 1×SSC, 0.1% SDS, 60° C., preferably at 1×SSC, 65° C., and more preferably at 0.5×SSC, 65° C.

The gene, which is hybridizable under the condition as described above, includes those having a stop codon generated in a coding region of the gene, and those having no activity due to mutation of active center. However, such mutants can be easily removed by ligating the gene with a commercially available activity expression vector, and measuring the GMP synthetase activity in accordance with the method described above.

The protein of the present invention is a protein encoded by the aforementioned DNA of the present invention, and has the amino acid sequence shown in SEQ ID NO: 2. The protein of the present invention may have an amino acid sequence of SEQ ID NO: 2 including substitution, deletion, insertion, addition or inversion of one or several amino acids, so long as it has GMP synthetase activity.

The GMP synthetase of the present invention has an activity for catalyzing the reaction that generates GMP from XMP. In this reaction, it can utilize L-glutamine and $(NH_4)_2SO_4$ as an amino group donor. The measured Km values for L-glutamine and ammonia of the GMP synthetase of the present invention were about 9.6 mM and 8.2 mM, respectively.

Moreover, when L-glutamine was used as an amino group donor, the GMP synthetase of the present invention showed the maximum activity around pH 6.5. When ammonia was used as the amino group donor with a constant amount of $(NH_4)_2SO_4$, which was added as a source of the amino group donor, it showed the maximum activity around pH 8.0 to 9.0. The GMP synthetase of the present invention was stable for at least 15 minutes at up to about 23° C.

In a transformant which is introduced with the DNA of the present invention in a form that allows expression of the GMP synthetase encoded by the DNA, the GMP synthetase activity is enhanced compared with a cell that is not transformed with it.

The "coryneform bacteria" includes bacteria having been hitherto classified into the genus Brevibacterium but united into the genus Corynebacterium at present (*Int. J. Syst. Bacteriol.*, 41, 255 (1981)), and include bacteria belonging to the genus Brevibacterium closely relative to the genus Corynebacterium. Examples of such coryneform bacteria include the followings.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes* (*Corynebacterium ammoniagenes*)
*Brevibacterium album*
*Brevibacterium cerinum*
*Microbacterium ammoniaphilum*

Specifically, the following strains of these bacteria are exemplified:

*Corynebacterium acetoacidophilum* ATCC13870
*Corynebacterium acetoglutamicum* ATCC15806
*Corynebacterium alkanolyticum* ATCC21511
*Corynebacterium callunae* ATCC15991
*Corynebacterium glutamicum* ATCC13020, 13032, 13060
*Corynebacterium lilium* (*Corynebacterium glutamicum*) ATCC15990
*Corynebacterium melassecola* ATCC17965
*Corynebacterium thermoaminogenes* AJ12340 FERM BP-1539)
*Corynebacterium herculis* ATCC13868
*Brevibacterium divaricatum* (*Corynebacterium glutamicum*) ATCC14020
*Brevibacterium flavum* (*Corynebacterium glutamicum*) ATCC13826, ATCC14067
*Brevibacterium immariophilum* ATCC14068
*Brevibacterium lactofermentum* (*Corynebacterium glutamicum*) ATCC13665, ATCC13869
*Brevibacterium roseum* ATCC13825
*Brevibacterium saccharolyticum* ATCC14066
*Brevibacterium thiogenitalis* ATCC19240
*Corynebacterium ammoniagenes* (*Brevibacterium ammoniagenes*) ATCC6871
*Brevibacterium album* ATCC15111
*Brevibacterium cerinum* ATCC15112
*Microbacterium ammoniaphilum* ATCC15354

These strains can be provided from, for example, the American Type Culture Collection. Each strain is assigned its registration number, and one can request provision of each strain by referring to its registration number. The registration numbers corresponding to the strains are indicated on the catalog of the American Type Culture Collection (Address: 12301 Parklawn Drive, Rockville, Md. 20852, United States of America). The AJ12340 strain was deposited at the National Institute of Bioscience and Human-Technology, Agency of Industrial Science and Technology, Ministry of International Trade and Industry (zip code: 305-8566, 1-3 Higashi 1-Chome, Tsukuba-shi, Ibaraki-ken, Japan) under the provisions of the Budapest Treaty, and received an accession number of FERM BP-1539.

The DNA of the present invention is preferably ligated to a vector DNA autonomously replicable in a cell of *Escherichia coli* and/or coryneform bacteria to form a recombinant DNA. By introducing this recombinant DNA into an *Escherichia coli* cell, the subsequent procedure can be made easy. The vector autonomously replicable in *Escherichia coli* cells is preferably a plasmid vector autonomously replicable in the host cell, and examples thereof include pUC19, pUC18, pBR322, pHSG299, pHSG399, pHSG398, RSF1010 and so forth.

As the vector autonomously replicable in coryneform bacterium cells, there can be mentioned pAM330 (refer to Japanese Patent Laid-open (Kokai) No. 58-67699/1983), pHM1519 (refer to Japanese Patent Laid-open (Kokai) No. 58-77895/1983) and so forth. Moreover, if a DNA fragment having an ability to make a plasmid autonomously replicable in coryneform bacteria is taken out from these vectors and inserted into the aforementioned vectors for *Escherichia coli*, they can be used as a so-called shuttle vector autonomously replicable in both of *Escherichia coli* and coryneform bacteria. Examples of such a shuttle vector include those mentioned below. There are also indicated microorganisms which harbors each vector, and accession numbers thereof at the international depository are shown in the parentheses, respectively.

pAJ655 *Escherichia coli* AJ11882 (FERM BP-136)
  *Corynebacterium glutamicum* SR8201 (ATCC39135)
pAJ1844 *Escherichia coli* AJ11883 (FERM BP-137)
  *Corynebacterium glutamicum* SR8202 (ATCC39136)
pAJ611 *Escherichia coli* AJ11884 (FERM BP-138)
pAJ3148 *Corynebacterium glutamicum* SR8203 (ATCC39137)
pAJ440 *Bacillus subtilis* AJ11901 (FERM BP-140)
pHC4 *Escherichia coli* AJ12617 (FERM BP-3532)

In order to prepare recombinant DNA by ligating the gene coding for GMP synthetase and a vector which can function in a cell of coryneform bacterium, the vector is digested by restriction enzyme(s) corresponding to the termini of the gene coding for GMP synthetase. Ligation is generally performed by using a ligase such as T4 DNA ligase.

To introduce the recombinant DNA prepared as described above to a coryneform bacterium, any known transformation methods can be employed. For instance, employable are a method of treating recipient cells with calcium chloride so as to increase the permeability of DNA, which has been reported for *Escherichia coli* K-12 [see Mandel, M. and Higa, A., J. Mol. Biol., 53, 159 (1970)]; and a method of preparing competent cells from cells which are at the growth phase followed by introducing the DNA thereinto, which has been reported for *Bacillus subtilis* [see Duncan, C. H., Wilson, G. A. and Young, F. E., Gene, 1, 153 (1977)]. In addition to these, also employable is a method of making DNA-recipient cells into the protoplast or spheroplast which can easily take up recombinant DNAs followed by introducing the recombinant DNA into the cells, which is known to be applicable to *Bacillus subtilis*, actinomycetes and yeasts [see Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)]. The electric pulse method can be also applied (refer to Japanese Patent Publication Laid-Open No. 2-207791).

A microorganism that is transformed with the DNA of the present invention can be utilized for the production of GMP synthetase. Moreover, since a microorganism, for example *Brevibacterium lactofermentum*, transformed with the DNA of the present invention and has enhanced GMP synthetase activity is excellent in the ability to generate GMP from XMP, it can be used for the production of GMP by fermentation or enzymatic process utilizing bacterial cells.

According to the present invention, there is provided a GMP synthetase derived from *Brevibacterium lactofermentum* and a gene coding for it. The GMP synthetase can be used for the production of GMP. A transformant that harbors the gene can be used for the production of GMP synthetase or GMP.

BEST MODE FOR CARRYING OUT THE INVENTION

Hereafter, the present invention will be explained more specifically with reference to the following examples.

EXAMPLE 1

Isolation of GMP synthetase gene of
*Brevibacterium lactofermentum* (guaA)

Genes corresponding to guaA were previously cloned from several kinds of organisms such as *Escherichia coli, Bacillus subtilis, Corynebacterium ammoniagenes, Borrelia burgdorferi* and *Dictyostelium discoideum*. Based on alignment of GMP synthetases deduced from the nucleotide sequences of these genes, a plurality of regions conserved in the enzymes were discovered. Then, a part of the guaA gene of *Brevibacterium lactofermentum* was obtained by PCR on the basis of the amino acid sequences of these conserved regions.

The PCR primers were designed by selecting such a region that the number of corresponding codons should become as few as possible, and referring to occurring frequency of the codons in *Brevibacterium lactofermentum*. The sequences of produced primers are shown below. In the following sequences, Y represents mixture of T and C, R represents mixture of G and A, and W represents mixture of A and T.

(1) Primer 1
    5'-WTCCCAWTCGATRGT-3'      (SEQ ID NO: 3)

(2) Primer 2
    5'-CACCACAACGTYGGY-3'      (SEQ ID NO: 4)

(3) Primer 3
    5'-RCCRACGTTGGGTG-3'       (SEQ ID NO: 5)

(4) Primer 4
    5'-TGGATGTCYCACGGY-3'      (SEQ ID NO: 6)

(5) Primer 5
    5'-TGGATGAGCCACGGY-3'      (SEQ ID NO: 7)

PCR was performed by using the aforementioned primers and chromosomal DNA of the *Brevibacterium lactofermentum* ATCC13869 strain as a template. Reaction conditions are shown in Table 1.

TABLE 1

| PCR reaction condition | | | |
|---|---|---|---|
| Reaction | Primer | Reaction condition | Cycle number |
| 1 | 1, 2 | 94° C. for 30 seconds, 45° C. for 30 seconds, 72° C. for 2 minutes | 30 |
| 2 | 1, 2 | 94° C. for 30 seconds, 45° C. for 30 seconds, 72° C. for 2 minutes | 40 |
| 3 | 4, 5, 1 | 94° C. for 30 seconds, 45° C. for 30 seconds, 72° C. for 2 minutes | 40 |
| 4 | 4, 5, 3 | 94° C. for 30 seconds, 45° C. for 30 seconds, 72° C. for 2 minutes | 40 |

As a result of the aforementioned PCR, no reaction product with the desired size was obtained in Reaction 1. In Reactions 2, 3, and 4, reaction products having sizes of about 0.5 kbp, about 1.2 kbp and about 0.7 kbp, respectively, were obtained. However, production of a plurality of reaction products with sizes other than the target sizes was observed in each of Reactions 2, 3 and 4. Therefore, each reaction product was separated by agarose gel electrophoresis, and only the reaction product with the target size were recovered.

Each of the recovered reaction products was ligated to TA cloning vector (Invitrogen). By using the obtained recombinant plasmid as a template, the nucleotide sequence of each PCR product was determined. In this experiment, the PCR products of about 0.5 kbp and about 1.2 kbp among the aforementioned PCR products were used as templates for the nucleotide sequence determination. The nucleotide sequence was determined by using Big Dye Terminator Cycle Sequencing Kit (Perkin Elmer) and Genetic Analyzer 310 (Perkin Elmer).

As a result, it was found that the fragment of about 1.2 kbp overlapped the fragment of about 0.5 kbp, and the amino acid sequence deduced from the nucleotide sequence of the obtained region showed high homology to the amino acid sequences of known GMP synthetases derived from other organisms. Therefore, it was determined that the PCR products obtained above were highly possibly parts of the target gene.

Therefore, it was then attempted to obtain upstream and downstream regions of the obtained region. They were obtained by the cassette-ligation mediated PCR (*Molecular and Cellular Probes*, 6, 467–475). The actual operation was performed by using a TaKaRa LA PCR in vitro Cloning Kit (Takara Shuzo) according to the instruction attached to the kit.

The PCR primers used for obtaining the upstream region, which were specific for the known region, were:

5'-TGCTCTAGACCTGCGATCTCAGTGAGGAAG-3' (SEQ ID NO: 8) for the first reaction, and 5'-CAGGGTGGTACTGCACGCCAGCCATTTTGC-3' (SEQ ID NO: 9) for the second reaction.

The PCR primers used for obtaining the downstream region, which were specific for the known region, were: 5'-CTCTGTTGGAGTCCAAGGTGACGGCCGCAG-3' (SEQ ID NO: 10) for the first reaction, and 5'-GTATCTTCCGAAGACGCAATGACCGCCGAC-3' (SEQ ID NO: 11) for the second reaction.

The cassettes used were those for EcoRI, HindIII, PstI, SalI and XbaI. Each cassette was ligated to chromosomal DNA of the *Brevibacterium lactofermentum* ATCC13869 strain that was digested with a restriction enzyme corresponding to each of those cassettes, and PCR was performed by using aforementioned primers and cassette primers attached to the aforementioned kit. As a result, when cassettes for EcoRI, HindIII, PstI, and SalI were used in the reactions aiming at obtaining upstream regions, reaction products of about 1.5 kbp, about 0.5 kbp, about 1.5 kbp and about 1.0 kbp, respectively, were obtained. When nucleotide sequences of these products were determined, it was found that all of the products contained the same sequence.

Further, when cassettes for EcoRI, HindIII and XbaI were used in the reactions aiming at obtaining downstream regions, reaction products of about 1.2 kbp, about 0.5 kbp and about 1.2 kbp, respectively, were obtained. When nucleotide sequences of these products were determined, it was found that all of the products contained the same sequence.

The sequences obtained as described above were ligated taking into account the overlap regions to obtain a sequence which consisted of 3390 bases containing a region which could code for a protein consisting of 523 amino acid residues. This protein consisting of the 523 amino acid residues showed high homology to the amino acid sequences of known GMP synthetases derived from other organisms over the full length. Therefore, it was considered that the target guaA gene could be obtained. The homology between the thus obatined guaA gene and *E. coli* guaA determined by Lipman-Pearson method (*Science*, Vol.227, 1435–1441 (1985) is 55.7% in the nucleotide sequence level.

EXAMPLE 2

Expression of *Brevibacterium lactofermentum* guaA in *Escherichia coli*

In order to confirm that the gene obtained in Example 1 was the target guaA gene, that gene was introduced into *Escherichia coli,* and expressed. From the transformant, a cell-free extract was prepared, and its GMP synthetase activity was confirmed. The expression of the guaA gene in *Escherichia coli* was performed as follows.

PCR primers each added with the SD (Shine-Dalgarno) sequence and a restriction enzyme recognition site were designed based on the sequence obtained in Example 1. By using these primers and chromosomal DNA of *Brevibacterium lactofermentum* ATCC13869 as a template, PCR was performed. The sequences of the primers used above are shown below.

```
5'-CTCGTCGACAAGGAAAAAGACGTATGAGCCTTCAGACAAATCATCGCCC-3'    (SEQ ID NO: 12)

5'-CTCGCATGCTTAATCCCATTCGATGGTTCCTGGTGGCTTGGAGGTTACGTCC-3' (SEQ ID NO: 13)
```

The obtained PCR product was digested with restriction enzymes that could digest the restriction sites added to the primers, and ligated to a vector, pUC18 (Takara Shuzo), digested with the same restriction enzymes. In this case, the target gene was ligated in the forward direction as to the direction of transcription by lac promoter present in the vector. *Escherichia coli* JM109 was transformed with the plasmid produced as described above.

The obtained transformant was cultured overnight in LB medium containing 50 μg/ml of ampicillin and 1 mM IPTG with shaking, then collected by centrifugation, and washed with Buffer A (20 mM potassium phosphate buffer (pH 7.5), 1 mM dithiothreitol (DTT)). The washed cells were suspended in the same buffer, and disrupted by sonication. After the sonication, cells not disrupted and other substances were removed by centrifugation to obtain a cell-free extract.

Measurement of GMP synthetase activity of the cell-free extract was performed in Reaction mixture A having the following composition: 100 mM Tris-HCl, pH 8.3, 1 mM DTT, 25 mM XMP, 25 mM ATP, 50 mM $MgCl_2$ and 50 mM L-glutamine. The reaction was allowed at 30° C. for 10 minutes, and then stopped by addition of 50-fold volume of 100 mM EDTA. Analysis and quantification of the reaction product were performed by HPLC. Analysis condition was as follows.

Column: Asahipak GS-220 (diameter: 7.6 mm, 50 cm)

Eluate: 0.2 M $NaH_2PO_4$ (pH 3.98)

Temperature: 50° C.

Flow rate: 1.5 ml/minute

Detection: UV absorption (254 nm)

The quantification of proteins was performed by using Protein Assay Kit (Bio-Rad Laboratories). When the GMP synthetase activity of the prepared cell-free extract was measured with these conditions, conversion of XMP into GMP was observed with a cell-free extract prepared from the strain which was introduced with the obtained gene. Thus, the target activity was confirmed.

EXAMPLE 3

Characterization of *Brevibacterium lactofermentum* guaA gene product

Production of GMP from XMP was also observed in a reaction utilizing, as a GMP synthetase source, a cell-free extract prepared from *Escherichia coli* JM109 in which the guaA gene described in Example 2 was expressed, and utilizing $(NH_4)_2SO_4$ instead of L-glutamine so that ammonia should be the amino group donor. Then, Km values of the enzyme were determined for the amino group donors, L-glutamine and ammonia. As a result, Km values for L-glutamine and ammonia were 9.6 mM and 8.2 mM, respectively. That is, substantially the same values were obtained for the both substrates.

The ammonia concentration was calculated in accordance with the equation of Henderson-Hasselbach using pKa of ammonia, 9.3, and pH of reaction mixture, 8.0. When pH characteristics of the enzyme was determined, the maximum activity was observed around pH 6.5 with L-glutamine as the amino group donor, and around pH 8.0–9.0 with ammonia as the amino group donor, which was supplied by a constant amount of $(NH_4)_2SO_4$.

Figure 1:
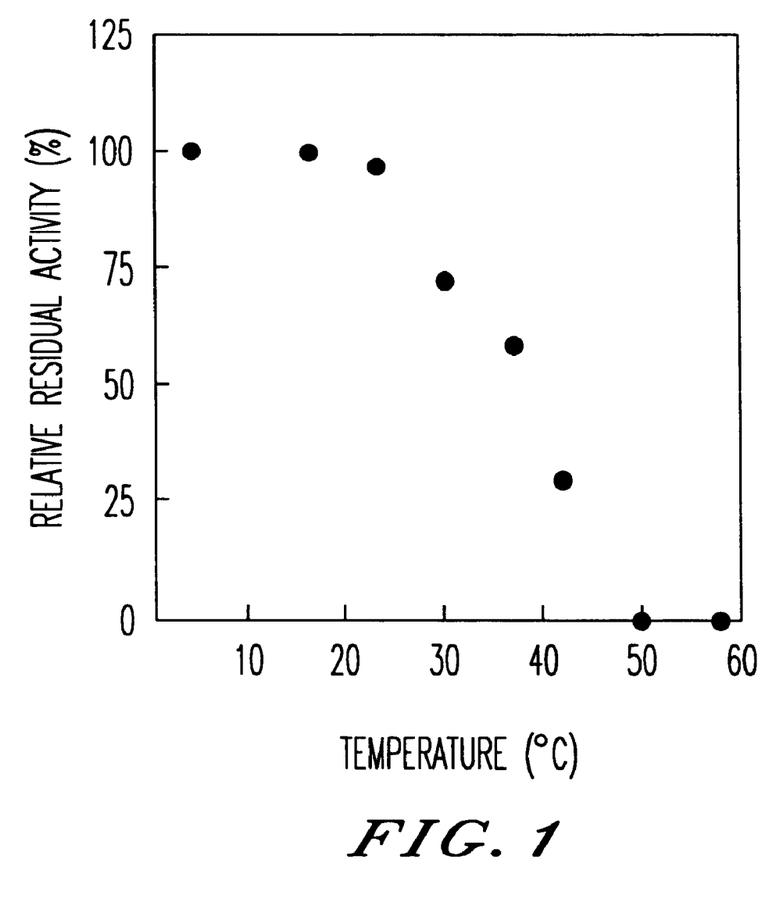
FIG. 1 graphically shows thermostability of GMP synthetase of the present invention.

When the thermostability of the enzyme was examined, the result shown in FIG. 1 was obtained. The thermostability was determined by maintaining a cell-free extract at each temperature shown in FIG. 1 for 15 minutes, then measuring residual activity at 30° C., and calculating a relative activity to the activity obtained by using a cell-free extract maintained at 4° C. As shown in FIG. 1, the enzyme was stable at least up to 23° C.

---

What is claimed is:

1. An isolated protein defined as follows:
   (A) a protein which has the amino acid sequence of SEQ ID NO: 1, or
   (B) a protein which has at least 90% homology to the amino acid sequence of SEQ ID NO: 2 and has a GMP synthetase activity.

2. The isolated protein according to claim 1, which is encoded by a nucleotide sequence (A) or (B):
   (A) nucleotides 887 to 2455 in SEQ ID NO: 1; or
   (B) a nucleotide sequence which hybridizes under stringent conditions to nucleotides 887 to 2455 in SEQ ID NO: 1, and codes for a protein having GMP synthetase activity, wherein said stringent conditions comprise washing in 1×SSC, and 0.1% SDS at 60° C.

3. The isolated protein according to claim 2, which is encoded by (A).

4. The isolated protein according to claim 2, which is encoded by (B).

5. The isolated protein according to claim 1, which is (A).

6. The isolated protein according to claim 1, which is (B).

7. The isolated protein according to claim 2, wherein the nucleotide sequence is not less than 90% homologous with nucleotides 887 to 2455 of SEQ ID NO: 1.

* * * * *